(12) United States Patent
Schmolz

(10) Patent No.: US 9,176,116 B2
(45) Date of Patent: Nov. 3, 2015

(54) CELL CULTURE SYSTEM FOR DETERMINING THE SENSITIZING, ALLERGENIC AND/OR IRRITATING EFFECT OF A SUBSTANCE

(75) Inventor: Manfred Schmolz, Reutlingen (DE)

(73) Assignee: HOT Screen GmbH (DE)

( * ) Notice: Subject to any disclaimer, the term of this patent is extended or adjusted under 35 U.S.C. 154(b) by 0 days.

(21) Appl. No.: 13/361,628

(22) Filed: Jan. 30, 2012

(65) Prior Publication Data

US 2012/0129162 A1    May 24, 2012

Related U.S. Application Data

(63) Continuation of application No. 12/556,274, filed on Sep. 9, 2009, now abandoned.

(60) Provisional application No. 61/095,834, filed on Sep. 10, 2008.

(51) Int. Cl.
*G01N 33/53* (2006.01)
*G01N 33/50* (2006.01)

(52) U.S. Cl.
CPC ........ *G01N 33/5047* (2013.01); *G01N 33/5082* (2013.01)

(58) Field of Classification Search
None
See application file for complete search history.

(56) References Cited

U.S. PATENT DOCUMENTS

2001/0049115 A1    12/2001    Collins et al.

FOREIGN PATENT DOCUMENTS

WO    WO 02/051358 A2    7/2002

OTHER PUBLICATIONS

Davies et al (Clinical Experimental Allergy, 2004. vol. 34, pp. 429-436).*
Kojima et al (AATEX, 2006. vol. 11, No. 3, pp. 177-187).*
Verhagen et al (Journal of Allergy Clinical Immunology 2006; Col. 117, pp. 176-183).*
International Search Report and Written Opinion mailed Jan. 25, 2010 in International Application No. PCT/US2009/056348.
Hsia, E. et al., "Effects of Topically Applied Acitretin in Reconstructed Human Epidermis and the Rhino Mouse," Journal for Investigative Dermatology, vol. 128, No. 1, Jan. 2008, pp. 125-130.
Noel-Hudson, M.S. et al., "Human Epidermis Reconstructed on Synthetic Membrane: Influence of Experimental Conditions on Terminal Differentiation," In vitro Cellular & Development Biology—Animal, vol. 31, No. 7, Jul. 1, 1995, pp. 508-515.

* cited by examiner

*Primary Examiner* — Celine Qian
(74) *Attorney, Agent, or Firm* — DLA Piper LLP (US)

(57) ABSTRACT

The present invention refers to a cell culture system especially for investigating the sensitizing, allergenic and/or irritating effect of substances, comprising a first and a second compartment that can communicate with each other via a permeable interlayer, whereby the first compartment has an epidermis model and the second a cell culture based on immune cells.

19 Claims, No Drawings

CELL CULTURE SYSTEM FOR DETERMINING THE SENSITIZING, ALLERGENIC AND/OR IRRITATING EFFECT OF A SUBSTANCE

CROSS-REFERENCE TO RELATED APPLICATIONS

This application is a continuation of Ser. No. 12/556,274, filed Sep. 9, 2009, pending, which claims benefit of 61/095,834, filed Sep. 10, 2008, which are hereby incorporated by reference in their entirety.

BACKGROUND OF THE INVENTION

Allergy is a disorder of the immune system that is inclusive of atopy. Allergic reactions occur in response to environmental substances known as allergens; these reactions are acquired, predictable and rapid. Allergy is characterized by excessive activation of certain white blood cells, called mast cells, and basophils by a type of antibody, known as IgE, resulting in an extreme inflammatory response. Common allergic reactions include eczema, hives, hay fever, asthma, food allergies, and reactions to the venom of stinging insects such as wasps and bees.

Different types of allergens are known. Inhaled allergens include dust or aerosols, e.g., pollen or house dust. Food allergens are substances contained in food to which the body reacts by hypersensitization (allergic reactions). Medicinal product allergens comprise certain active substances in medicinal products, for example antibiotics or analgesics. A particularly important group of allergenic substances are the contact allergens. These can cause an allergic reaction in those affected through skin contact. Certain metals and odoriferous substances belong among the contact allergens.

In recent decades, especially in the Western industrial countries a sudden rise in the number of allergens has been observed. Many allergenic substances are ingredients of cosmetics or other topically applied substances (compositions for local external application). Cosmetics or topical agents are tested for their allergenic properties by means of experiments on animals. The findings thus gained, however, are only of limited value because experimental animals do not always react to the same allergens as human beings and vice versa. This situation frequently gives rise to false positive and false negative results. Meanwhile there are also practical and ethical concerns associated with animal testing.

In light of the state of testing for allergenic activity, there is a need for effective new tools and methods for determining allergenic activity.

SUMMARY

The present invention relates generally to a cell culture system for determining the sensitizing, allergenic and/or irritating effect of various substances.

In one embodiment, the present invention is directed to a cell culture system for determining the sensitizing, allergenic and/or irritating effect of substances, comprising: a) a first compartment comprising an epidermis model; and b) a second compartment comprising a cell culture based on immune cells, wherein the first and second compartments are separated by a permeable interlayer, and wherein an allergen or irritating agent introduced into the first compartment activates the immune cells of the second compartment. In a particular embodiment, the immune cells are antigen presenting cells, e.g., macrophages and/or dendritic cells. In a particular embodiment, the immune cells are lymphocytes, in particular B lymphocytes and/or T lymphocytes. In a particular embodiment, the immune cells show matching tissue compatibility antigens. In a particular embodiment, the immune cell culture is substantially free of tissue cells. In a particular embodiment, the immune cells are derived from a human. In a particular embodiment, the immune cells are isolated from blood. In a particular embodiment, the epidermis model has a layered structure. In a particular embodiment, the epidermis model is multilayered, e.g., the epidermis model can comprise at least one epidermis layer selected from the group consisting of: stratum corneum, stratum lucidum, stratum granulosum, stratum spinosum and stratum basale. In a particular embodiment, the epidermis model comprises live epidermis cells, e.g., keratinocytes. In a particular embodiment, the epidermis model is substantially free of immune cells. In a particular embodiment, the epidermis model is an animal epidermis model, e.g., a human epidermis model. In a particular embodiment, the one or more substances comprise at least one cosmetic agents. In a particular embodiment, the one or more substances comprise at least one pharmacologically active medicinal agent. In a particular embodiment, the second compartment is filled with an aqueous medium.

In one embodiment, the present invention is directed to a method of using any of the cell culture systems described herein to examine the sensitizing, allergenic or irritating effect of one or more substances, comprising contacting the first compartment with the substance and detecting an allergenic response in the second compartment.

In one embodiment, the present invention is directed to a method for examining the sensitizing, allergenic and/or irritating effect of an agent, comprising: a) contacting the surface of an epidermis model contained in a first compartment with the agent; and b) determining the activity of a cell culture of immune cells contained in a second compartment, wherein the first compartment and second compartment are separated by a permeable interlayer, wherein the presence of an activated immune cell in the second compartment indicates that the agent is an allergen or irritating agent. In a particular embodiment, the immune cells are isolated from blood. In a particular embodiment, the cell culture comprises antigen presenting cells and lymphocytes. In a particular embodiment, the antigen presenting cells are derived from monocytes under differentiating conditions. In a particular embodiment, the activity of the immune cells is determined by examining the supernatant of the cell culture. In a particular embodiment, the activity of the immune cells is determined by assaying for substances produced by activated immune cells. In a particular embodiment, the substances produced by activated immune cells are selected from the group consisting of: signal transducers, receptors, enzymes and antibodies. In a particular embodiment, the activity of the immune cells is determined by assaying for messenger substances from keratinocytes of the epidermis model. In a particular embodiment, the activity of the immune cells is determined by identifying proliferation of the immune cells. In a particular embodiment, the activity of the immune cells is determined by measuring surface markers of the immune cells. In a particular embodiment, the activity of the immune cells is determined by measuring signal transduction components of the immune cells. In a particular embodiment, the activity of the immune cells is determined by measuring intracellular cytokines of the immune cells. In a particular embodiment, the activity of the immune cells is determined by analyzing messenger RNA levels within the immune cells.

DETAILED DESCRIPTION

The present invention is directed to providing an extracorporeal investigation model specifically for allergens. As used herein, an "allergen" is a non-parasitic antigen capable of stimulating a hypersensitivity reaction in individuals. Described herein are materials and methods that satisfactorily mimic the complex physiological situation in a subject, e.g., a human, that can lead to an allergy, while avoiding the disadvantage known from the current state of the art, but at the same time giving consideration to the current developments in the field of approval tests for cosmetics and topical agents.

Described herein is a cell culture system useful for investigating the sensitizing, allergenic and/or irritating effect of substances, comprising a first and a second compartment such that communication is allowed between the first and second compartment. The first compartment contains an epidermis model, and the second compartment contains immune cells. The communication between the two compartments is made possible by separating the compartments with a permeable interlayer. As used herein, "communication" refers to molecular communication between cells of the two compartments, e.g., through passing of messengers or signaling molecules, e.g., chemokines, cytokines or sensitizing, allergenic and/or irritating substances, between the two compartments. It in one embodiment, the first compartment contains only the epidermis model, and the second compartment contains only the cell culture based on the immune cells.

The invention provides a cell culture system that is primarily suitable for investigating contact allergens and irritants. For this purpose the epidermis model of the first compartment is particularly advantageous as a model structure for natural skin. In such a situation, the epidermis model with the permeable interlayer provide a model for assessing the activity of contact allergens. If a substance is introduced into the first compartment comprising the epidermis model, and the substance is an allergen, then the substance or signals triggered by that substance will be sent to the second compartment that activate the immune cells. As used herein, "activate" means any number of alterations to the state of the cell such that it mimics and in vivo activated immune cell (e.g., expansion of the immune cell population, production and/or release of specific molecular signals, change in the content of the cell surface receptors, change in gene expression patterns, and other measurable changes known to one of skill in the art).

Activation of immune cells can be determined by assessing, for example, proliferation of immune cells and in the production and excretion of messenger substances and immunoglobulins, especially of immunoglobulin E (IgE). Where the immune cells of the cell culture system have had contact with the substances to be examined, their presence in the second compartment, assuming that they are of an allergenic nature, causes the immune reaction described above to become more intensive. These processes can be recorded and evaluated to identify an allergen or the degree of allergenicity.

In the cell culture system the proximity of the epidermis model to the immune cells is a reflection of the natural configuration of skin and immune system. In the cell culture system the immune cells of the second compartment are separated from the epidermis model in the first compartment by the interlayer. This arrangement can prevent inadvertent reactions between the epidermis model and the immune cells, which might otherwise interfere with the examination of the substances. The cellular epidermis model and the immune cells, therefore, can be of different origin and, in particular, they can originate from different donors.

In one embodiment, the immune cells are antigen presenting cells (APCs), e.g., macrophages and/or dendritic cells. APCs are useful because they are involved in the presentation of allergens to other cells of the immune system. Allergen presentation causes allergen-specific lymphocytes to be activated. Activation of this kind manifests itself in particular as a proliferation of cells and in the production and excretion of messenger substances and immunoglobulins, especially of IgE. Allergen-specific T lymphocytes, together with the IgE, make contributions to the initial identification of or, if appropriate, to the re-identification, of allergenic substances.

The immune cells of the second compartment can be precursor cells of APCs. Monocytes, for example, can be considered as suitable precursor cells, if they are allowed to differentiate under specific conditions into APCs. One of skill in the art familiar with culturing monocytes would realize that precursor cells can be matured into cells useful in the cell culture system. To achieve differentiation, for example, the precursor cells can be incubated in the presence of various cytokines known to specifically induce differentiation. The precursor cells can be incubated, for example, to produce macrophages in the presence of M-CSF or G-CSF. For the purpose of differentiation into dendritic cells, the precursor cells can be incubated in the presence of, inter alia, GM-CSF and IL-4, or others. The differentiation can be implemented, for example, over a period of about 5 to about 20 days, for a period of about 7 to 18 days, or for a period of about 10 to 14 days.

The immune cells of the second compartment can be lymphocytes, e.g., B lymphocytes and/or T lymphocytes. Both the B lymphocytes and the T lymphocytes are of importance for the initial identification and for re-identification of allergenic substances. In one embodiment, the cell culture of the second compartment is one comprising APCs, B lymphocytes and T lymphocytes.

The immune cells can exhibit, for example, matching tissue compatibility antigens (major histocompatibility complex (MHC) antigens). This makes it possible to avoid rejection responses between the immune cells. Rejection responses of this kind would otherwise make it difficult to investigate sensitizing, allergic and/or irritating responses that might be taking place. Moreover, a correct antigen presentation only takes place if the MHC antigens of the APC and of the B and T lymphocytes to be sensitized actually are identical, e.g., derived from the same donor.

The cell culture of the second compartment can comprise tissue cells. Suitable tissue cells are, for example, keratinocytes and/or fibroblasts. The tissue cells can also be primary isolates. Alternatively, the cell culture of the second compartment can be substantially free of tissue cells.

The immune cells can be derived, for example, from one donor, in particular from one and the same donor. In a particular embodiment, the immune cells are isolated from blood, primarily from patient blood. The immune cells can be isolated from the blood of healthy persons or from those with a disposition for allergies.

In a particular embodiment, the cell culture system involves only cells of human origin. This makes it possible to simulate the in vivo situation of the human organism in a particularly effective manner. In this way it is possible to further enhance the validity of the results gained with the aid of the cell culture system with regard to a sensitizing, allergenic and/or irritating effect on humans. The cells of the cell culture system, particularly the cells of the epidermis model and/or the immune cells, can be propagated as cell lines.

In one embodiment, the immune cells are isolated from a subject's blood. In particular, the immune cells can be isolated with the aid of tools and methods known in the art, particularly with the aid of centrifugation techniques. One centrifugation technique to be considered, for example, is density centrifugation. Other centrifugation techniques, however, can also be used. Alternatively, the immune cells can be isolated by means of suitable sorting methods, for example magnetic beads and/or fluorescence-activated cell sorting (FACS) methods.

The cellular epidermis model can comprise individual epidermis cells, e.g., keratinocytes. The epidermis model has a layered, e.g., a multilayered structure. In particular, the epidermis model can have a differentiated multilayered structure. In a further version the epidermis model manifests at least one epidermis layer from the stratum corneum, stratum lucidum, stratum granulosum, stratum spinosum and stratum basale group. The epidermis model involves primarily living epidermis cells, in particular living keratinocytes. The epidermis model can consist of a corneous surface and the epidermal keratinocyte layers below it. In a particular embodiment, the epidermis model is substantially free of immune cells. The epidermis model can be of animal origin, preferably of human origin.

In addition to assessing the effect of substances on the activation of immune cells, certain substances with the relevant potential can trigger additional reactions, particularly in keratinocytes of the epidermis model, which significantly improves the detection of incompatibility reactions.

As used herein, a "sensitizing" effect of a substance refers to the triggering of a sensitization event. "Sensitization" herein refers to the immune reactions to which initial contact with the substance, particularly with an allergen, gives rise in a given organism. Primarily this initially entails the activation of a few B lymphocytes and T lymphocytes, which then multiply greatly (oligoclonal primary response). At the end of this activation process, most of the lymphocytes are eliminated by the immune system. Allergen-specific memory cells are formed, however, that continue to exist over extended periods in significantly higher numbers than the original allergen-specific cells.

An allergy arising as a result of sensitization is an excessive defense reaction of the immune system to a specific allergen, which may occur following a repeat contact with the relevant allergen. By contrast with primary sensitization, the excessive secondary immune reaction is caused by the many B lymphocyte and T lymphocyte memory cells with matching antigen receptors (oligoclonal secondary response). This means that this reaction is reinforced with each renewed contact with the allergen.

By contrast, an irritating effect stems from damage to tissue cells triggered by an irritant. In a first phase of irritation the tissue cells themselves release messenger substances, for example the lymphocyte activating factor interleukin-1 alpha (IL-1α) and the lymphocyte-derived neutrophil-activating peptide, also known as the chemokine interleukin-8 (IL-8). The released messenger substances attract immune system cells and activate them. If the irritating effect of the irritant continues and gets stronger, tissue cells die. This in turn causes the release of intracellular constituents (in the sense of a necrotic process). This enhances the secondary activation of immune system cells. The effects accompanying an irritation are primarily antigen-unspecific. Primarily it is macrophages and granulocytes that are involved.

The substance to be examined, i.e., the potential allergenic agent or irritant, can be, for example, a plant extract and/or oil, cosmetics and/or their constituents, or pharmacologically active dermatologicals (topicals), particularly medicinal products to be applied topically to the skin and/or other constituents.

In a further version the first compartment is designed as the upper compartment and the second compartment as the lower compartment of the cell culture system. The cell culture system, for example, can be designed in the manner of the commercially available permeable support systems (e.g. TRANSWELL® systems). At least the second compartment can contain a watery, i.e., aqueous, medium.

In a particular embodiment, the invention is directed to a process for examining the sensitizing, allergenic and/or irritating effect of substances, especially when using the cell culture system described herein. Such a method can comprise the steps of a) addition of the substance to be examined on the surface of an epidermis model that is in communication with a cell culture based on immune cells via a permeable interlayer, and b) examination of the cell culture for a sensitizing, allergenic and/or irritating response.

The supernatant of the cell culture can be examined, for example, to determine the activity state of the immune cells. Substances formed by the immune cells, e.g., messenger substances, signal transducers (signal transduction molecules or signal transduction components), receptors, enzymes and/or antibodies, for example, can be examined in the cell culture supernatant (cell culture media) or as intracellular components. The messenger substances (e.g., mediators) can be, for example, cytokines and/or chemokines. The concentration of messenger substances is primarily determined in the culture supernatant and/or in the cells. The density of the signal transducers and/or receptors is determined, for example, on and/or in the immune cells. The messenger substances can be, for example, interferon-γ (IFNγ), IL-4 and/or Eotaxin. Suitable receptors can be, for example, surface receptors. The receptors are surface receptors of the lymphocytes, e.g., CD25, CD69, CD152 and CD 154. Some examples of signal transducers are nuclear factor kappa beta (NFκβ), zeta-associated protein (ZAP-70) and nuclear factor of activated T cells (NFAT). Potentially suitable enzymes can be, for example, phospholipases, cyclooxygenases, protein kinases, poly ADP ribose polymerase (PARP), matrix metalloproteinases (MMP), tryptases, caspases, dipeptidyl peptidases, kinases and/or other important enzymes for the generation of signals. The antibodies are primarily IgE or IgG4.

The characteristics that indicate cellular activation by epidermis cells located in the epidermis model, particularly keratinocytes, can be assessed. Suitable investigation methods include, for example, electrophoretic processes, polymerase chain reaction (PCR), high pressure liquid chromatography (HPLC), array technologies, radiometric methods, histological staining techniques, flow cytometric methods and/or various different blotting methods. Electrophoretic methods include, for example, gel electrophoresis, e.g., two-dimensional polyacrylamide gel electrophoresis (2D page). Western blot analysis can also be used as a detection method. It is also possible to combine electrophoretic methods with blotting methods. Array technologies include, for example, the Immuno Solid-phase Allergen Chip (ISAC).

Antibodies formed by the immune cells can be detected by means of appropriate immunoassays. Examples for immunoassays include, for example, enzyme-linked immunosorbent assay (ELISA) and radio allergosorbent test (RAST).

Substances secreted by the immune cells can also be detected to determine the state of activation of immune cells. The secreted substances can be, for example, proteins and/or peptides. The proteins can be, for example, receptors and/or proteins with enzymatic activity. The secreted substances can be, for example, glycosylated proteins and/or peptides. The secreted substances can be, for example, messenger substances. The messenger substances can be low or high molecular compounds. The messenger substances can be, for example, radical oxygen compounds, lipoid compounds, biogenic amines, cytokines, growth factors and/or chemokines, soluble receptors, or even membrane vesicles (e.g., exosomes).

Detection of secreted compounds can be accomplished by determining the concentration of the secreted substances in the supernatant of the cell culture. Techniques for detecting secreted substances are known to one of skill in the art. Secreted substances can be detected at the transcriptional level, the translational level and/or the post-translational level. The excreted substances can be examined with the aid of array technologies, especially with the aid of, for example, multiplex bead arrays or planar arrays.

Determining the activation state of immune cells can be accomplished, for example, by detecting proliferation of the immune cells, particularly lymphocytes. A first or repeated contact with an allergen particularly stimulates the B lymphocytes and T lymphocytes to proliferate.

The cell culture system described herein assesses the severity of allergenicity exhibited by a potential allergen. Methods described herein for identifying allergens can be quantitative. The data collected from various antigens/allergens can be compiled, for example, to determine a reference scale of allergenicity. The severity of an allergic response is determined by a model allergenic response, with the severity determined by measuring the factors described herein, e.g., cell expansion, detection of released factors, etc. Comparing the allergenic reaction produced by a potential allergen to the reference allergenic scale, for example, allows one of skill in the art to determine the degree of allergenicity caused by the potential allergen.

Ultimately, the present invention refers to the use of the cell culture system according to the invention for examining the sensitizing, allergenic and/or irritating effect of substances. There is a special benefit that makes the cell culture system suitable for discriminating between an allergy triggered by the examined substances and irritation. Equally, the cell culture system according to the invention is suitable for performing parallel examinations using multiple cell culture systems.

EXAMPLE

For preparing freshly-isolated keratinocytes, skin material obtained by surgical means is subjected to an enzymatic digestion process. Keratinocytes, for example, gained in this manner are then transferred to membrane-bottomed dishes (e.g., MILLIPORE MILLICELLS®) that serve as compartments. These culture vessels contain an appropriate culture medium containing fetal calf serum, penicillin, streptomycin, nonessential amino acids and growth factors for cultivating keratinocytes. The culture medium is regularly refreshed during the culturing of the cells until sufficient dimensional differentiation into an epidermis equivalent has taken place. The differentiated epidermis encompasses multiple cell layers, particularly proliferating, non-proliferating and corneous cell layers.

For the preparation of the immune cells, leukocytes, for example, are obtained from the peripheral blood of a subject. The cells are enriched via a Ficoll gradient. The leukocytes are then propagated in multiwell plates, which serve as compartments. Each multiwell plate contains a suitable proliferation medium that shows necessary additives such as, for example, plasma or serum, vitamins, and/or other essential components such as, for example, amino acids, nucleotides and antibiotics (e.g., penicillin, streptomycin, etc.).

The compartments with the differentiated epidermis cultures are fitted into the compartments with the leukocyte cultures, forming a cell culture system. The cell culture system is a co-culture with two different cell populations (e.g., epidermis cells and leukocytes), whereby the compartment with the epidermis culture represents the upper compartment and the compartment with the leukocytes the lower compartment. A substance (e.g., a potentially allergenic agent or irritant) to be examined is applied to the surface of the epidermis culture of the upper compartment. The co-culture is then incubated for a specific time. To determine the sensitizing potential the lymphocyte proliferation, the mediator synthesis of the lymphocytes and/or the parameters of the cell activation of the leukocytes in the lower compartment are measured. Additionally, the upper compartment can be examined for parameters for an irritation.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method of determining the sensitizing or allergenic effect of a substance, comprising:
    a) contacting a surface of an epidermis model contained in a first compartment of a culture apparatus with the substance;
    b) the activity of a cell culture of immune cells comprising antigen presenting cells contained in a second compartment of said apparatus; and
    c) determining that the substance has a sensitizing or allergenic effect if the second compartment comprises an activated immune cell,
    wherein the first compartment and second compartment are separated by a permeable interlayer and wherein the epidermis model is in communication with the cell culture of immune cells via the permeable interlayer.

2. The method of claim 1, wherein the immune cells are isolated from blood.

3. The method of claim 1, wherein the cell culture comprises antigen presenting cells and lymphocytes.

4. The method of claim 3, wherein the antigen presenting cells are derived from monocytes under differentiating conditions.

5. The method of claim 1, wherein measuring the activity of the cell culture of immune cells comprises examining the supernatant of the cells of the cell culture of immune cells.

6. The method of claim 1, wherein the activity of the cell culture of immune cells comprises assaying for substances produced by activated immune cells.

7. The method of claim 6, wherein the substances produced by activated immune cells are selected from the group consisting of: signal transducers, receptors, messengers, enzymes and antibodies.

8. The method of claim 1, wherein the epidermis model comprises keratinocytes, and wherein measuring the activity of the cell culture of immune cells comprises assaying for messenger substances from the keratinocytes of the epidermis model.

9. The method of claim 1, wherein measuring the activity of the cell culture of immune cells comprises identifying measuring proliferation of the immune cells.

10. The method of claim 1, wherein measuring the activity of the cell culture of immune cells comprises measuring surface markers of the immune cells.

11. The method of claim 1, wherein measuring the activity of the cell culture of immune cells comprises measuring signal transduction components of the immune cells.

12. The method of claim 1, wherein measuring the activity of the cell culture of immune cells comprises measuring intracellular cytokines of the immune cells.

13. The method of claim 1, wherein measuring the activity of the cell culture of immune cells comprises analyzing messenger RNA levels within the immune cells.

14. A method of determining the sensitizing or allergenic effect of a substance, comprising:
   a) contacting a surface of a multilayered epidermis model in a first compartment of a culture apparatus with the substance;
   b) measuring the activity of a cell culture of immune cells comprising antigen presenting cells and lymphocytes contained in a second compartment of said apparatus; and
   c) determining that the substance has a sensitizing or allergenic effect if the second compartment comprises an activated immune cell,
   wherein the first compartment and second compartment are separated by a permeable interlayer and wherein the multilayered epidermis model is in communication with the cell culture of immune cells via the permeable interlayer.

15. The method of claim 14, wherein measuring the activity of the cell culture of immune cells comprises measuring the oligoclonal primary response of the lymphocytes, wherein the presence of an oligoclonal primary response of the lymphocytes indicates that the substance has a sensitizing effect.

16. The method of claim 14, wherein measuring the activity of the cell culture of immune cells comprises determining the oligoclonal secondary response of the lymphocytes, wherein the presence of an oligoclonal secondary response of the lymphocytes indicates that the substance has an allergenic effect.

17. The method of claim 14, wherein the activity of the cell culture of immune cells comprises one or more of: assaying for substances produced by activated immune cells, measuring proliferation of the immune cells, measuring surface markers of the immune cells, measuring signal transduction components of the immune cells, measuring intracellular cytokines of the immune cells, or measuring messenger RNA levels within the immune cells.

18. A method of determining the allergenic effect of a substance, comprising:
   a) contacting a surface of a multilayered epidermis model in a first compartment of a culture apparatus with the substance, wherein the first compartment is separated from a second compartment containing a cell culture of immune cells comprising antigen presenting cells and lymphocytes by a permeable interlayer, wherein the multilayered epidermis model is in communication with the cell culture of immune cells via the permeable interlayer;
   b) contacting the surface of the multilayered epidermis model one or more additional times with the substance;
   c) measuring an oligoclonal secondary response of the cell culture of immune cells; and
   d) determining that the substance has an allergenic effect if the lymphocytes comprise the oligoclonal secondary response.

19. The method of claim 18, wherein measuring the oligoclonal secondary response of the cell culture of immune cells comprises one or more of: assaying for substances produced by activated immune cells, measuring proliferation of the immune cells, measuring surface markers of the immune cells, measuring signal transduction components of the immune cells, measuring intracellular cytokines of the immune cells, or measuring messenger RNA levels within the immune cells.

* * * * *